(12) United States Patent
Verhaegen et al.

(10) Patent No.: US 9,242,120 B2
(45) Date of Patent: Jan. 26, 2016

(54) TIME-RESOLVED PRE-TREATMENT PORTAL DOSIMETRY SYSTEMS, DEVICES, AND METHODS

(71) Applicant: VARIAN MEDICAL SYSTEMS INTERNATIONAL AG, Zug (CH)

(72) Inventors: Frans Verhaegen, Riemst (BE); Mark Podesta, Maastricht (NL); Sebastiaan M. J. J. G. Nijsten, Maastricht (NL); Lucas C. G. G. Persoon, CT Berg en Terblijt (NL); Christof Baltes, Oberwil-Lieli (CH); Stefan G. Scheib, Waedenswil (CH)

(73) Assignee: VARIAN MEDICAL SYSTEMS INTERNATIONAL AG, Zug (CH)

( * ) Notice: Subject to any disclaimer, the term of this patent is extended or adjusted under 35 U.S.C. 154(b) by 0 days.

(21) Appl. No.: 14/745,829

(22) Filed: Jun. 22, 2015

(65) Prior Publication Data
US 2015/0314140 A1 Nov. 5, 2015

Related U.S. Application Data

(63) Continuation of application No. 14/074,144, filed on Nov. 7, 2013, now Pat. No. 9,089,696.

(51) Int. Cl.
*A61N 5/10* (2006.01)

(52) U.S. Cl.
CPC ............ *A61N 5/1071* (2013.01); *A61N 5/1031* (2013.01); *A61N 5/1075* (2013.01); *A61N 2005/1054* (2013.01)

(58) Field of Classification Search
USPC .................................... 378/65, 62; 382/132
See application file for complete search history.

(56) References Cited

U.S. PATENT DOCUMENTS

2010/0119032 A1* 5/2010 Yan ..................... A61N 5/1049
378/4
2014/0105355 A1 4/2014 Toimela et al.

OTHER PUBLICATIONS

P.C. Williams, "IMRT: delivery techniques and quality assurance", The British Journal of radiology, 76 (2003), 766-776.
Winiecki et al., "The gamma evaluation method as a routine QA procedure of IMRT", Rep. Pract. Oncol. Radiother., 2009 14/5, 162-168.
Bailey et al., "EPID dosimetry for pretreatment quality assurance with two commercial systems", Journal of Applied Clinical Medical Physics, vol. 3, No. 4, 2012.
Fuangrod et al., "Development of EPID-based Real Time Dose Verification for Dynamic IMRT", World Academy of Science, Engineering and Technology, 56, 2011.
Fuangrod et al., "A system for EPID-based real-time treatment delivery verification during dynamic IMRT treatment", Med. Phys. 40 (9), Sep. 2013.
S. M. J. J. G. Nijsten et al. "A global calibration model for s-Si EPIDs used for transit dosimetry", Med. Phys. 34 (10), Oct. 2007.

(Continued)

*Primary Examiner* — Kiet T Nguyen
(74) *Attorney, Agent, or Firm* — Shapiro, Gabor and Rosenberger, PLLC

(57) ABSTRACT

Systems, devices, and methods for pre-treatment verification of radiation dose delivery in arc-based radiation therapy devices using a time-dependent gamma evaluation method.

20 Claims, 7 Drawing Sheets

(56) References Cited

OTHER PUBLICATIONS

Rowshanfarzad et al., "Measurement and modeling of the effect of support arm backscatter on dosimetry with a Varian EPID", Med. Phys. 37 (5), May 2010.

Ann Van Esch et al: "The use of an aSi-based EPID for routine absolute dosimetric pre-treatment verification of dynamic IMRT fields," Radiotherapy and Oncology, vol. 71, No. 2, May 2004, pp. 223-234, XP055087412, Section 2.1. The aSi-based EPID for dosimetry in dynamic mode.

* cited by examiner

FIG. 3

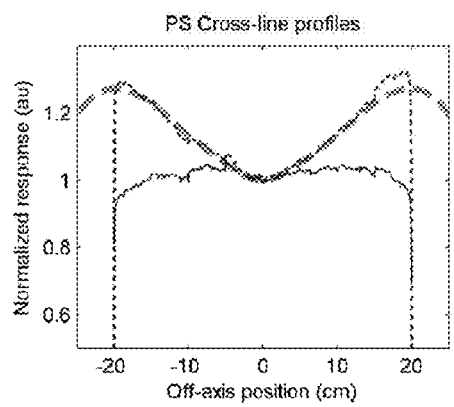

Pixel sensitivity (solid) derived via fitted ratio profile (dashed) and flood field profile (dotted).

FIG. 4

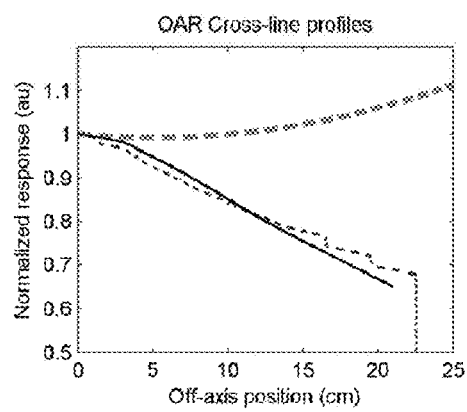

Fitted off axis ratio (dashed) derived via composite EPID profile (dotted) and ion chamber measured beam profile (solid)

FIG. 5

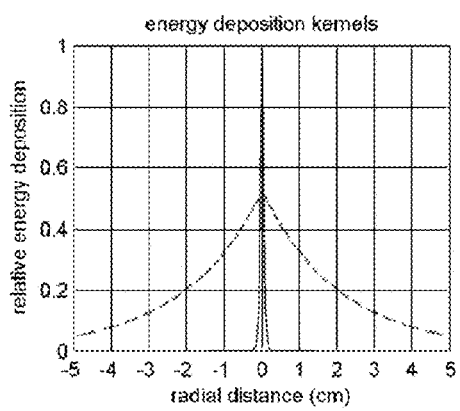

Diagram of energy deposition kernels.

FIG. 6

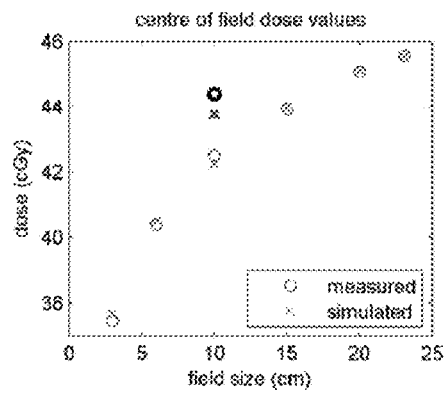

Measured and simulated point dose values from the centre of each square field. Bold markers indicate off-axis field.

Measured (solid) and simulated (dashed) in-line dose profiles for an on-axis and off-axis 10x10cm field FIG. 8
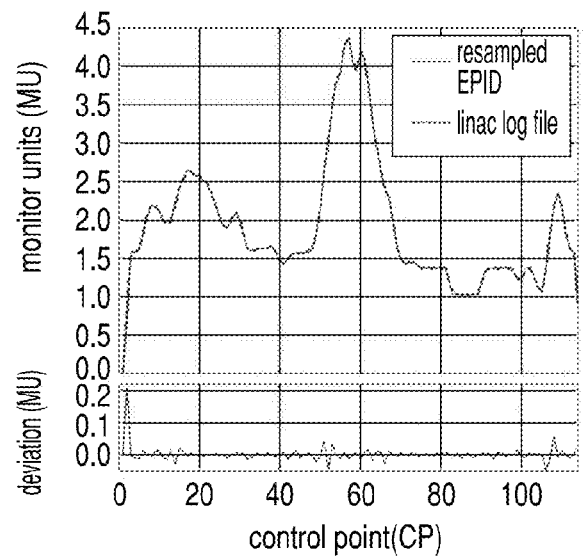
CP resampling MU check. The solid line is the
resampled EPID header values. The dashed line is the
linac log file values, the deviation from the log file is
shown in the bottom panel.
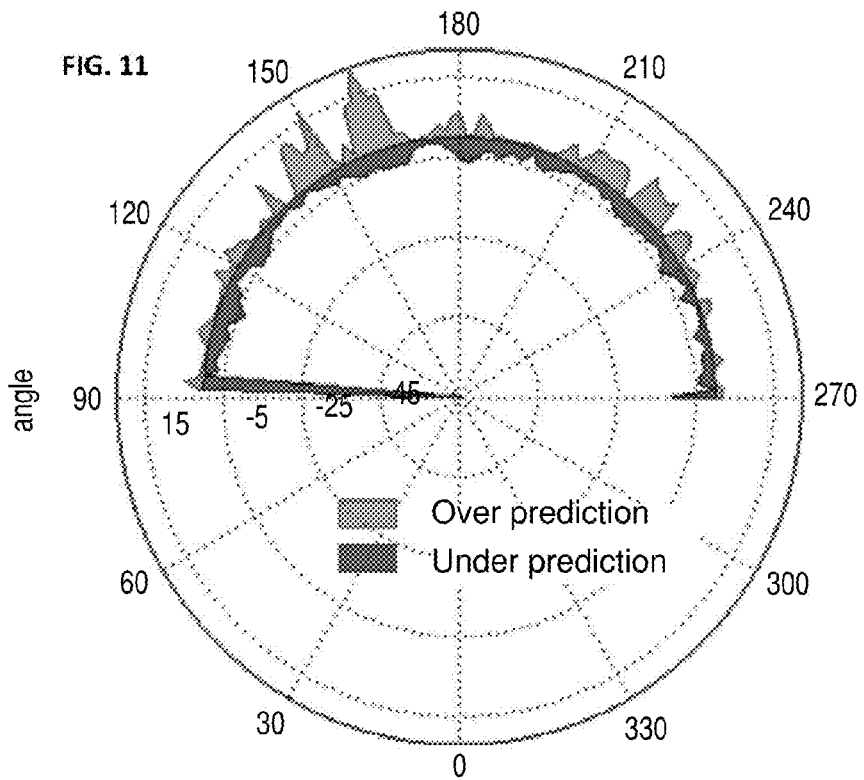
FIG. 11

Gamma distributions (3%, 3mm, 3sec) between measurement and
prediction of the differential (per CP) 2D portal dose images for a single
6MV FFF VMAT arc.

TIME-RESOLVED PRE-TREATMENT PORTAL DOSIMETRY SYSTEMS, DEVICES, AND METHODS

FIELD

The present disclosure relates generally to delivering radiation to a patient, and more particularly to systems, methods, and computer program products for providing time dependent pre-treatment dosimetric verification of dynamic radiation therapy treatments using an electronic portal imaging device (EPID). The present disclosure also relates to systems, methods, and computer program products for providing time-dependent gamma analysis on dynamic data.

BACKGROUND

Dynamic radiation treatment techniques, such as intensity-modulated radiation therapy (IMRT) and volumetric modulated arc therapy (VMAT), are typically used with a radiotherapy system, such as a linear accelerator (linac), equipped with a multileaf collimator (MLC) to treat pathological anatomies (tumors, lesions, vascular malformations, nerve disorders, etc.) by delivering prescribed doses of radiation (X-rays, gamma rays, electrons, protons, and/or ions) to the pathological anatomy while minimizing radiation exposure to the surrounding tissue and critical anatomical structures. Use of the multileaf collimator allows the radio therapist to treat a patient from multiple angles while varying the shape and dose of the radiation beam, thereby providing a greatly enhanced ability to deliver radiation to a target within a treatment volume while avoiding excess irradiation of nearby healthy tissue. Intensity-modulated radiation therapy (IMRT) and volumetric modulated arc therapy (VMAT), which are complex techniques involving the synchronous occurrence of gantry rotation, multileaf collimator motion, and dose rate modulation, are rapidly growing as radiation therapy techniques due to their ability to quickly deliver highly conformal dose distributions.

Because of the high complexity and uniqueness of (IMRT) and (VMAT) treatment plans, patient-specific pre-treatment (i.e., without the patient in the beam) verification is generally considered a necessary prerequisite to patient treatment. Pre-treatment verification includes procedures to compare the whole or at least part of the intended treatment plan with measurements of corresponding radiation beams delivered by the linear accelerator (linac) outside the patient treatment time.

Dosimetric verification is one of the pre-treatment protocols implemented for (IMRT) and (VMAT) treatments. Dosimetric verification includes verification that the dose distribution delivered is in fact the dose distribution predicted to be delivered to the patient. Because of the increased beam delivery complexity offered by (IMRT) and (VMAT) treatments, dosimetric verification for (IMRT) and (VMAT) treatments require rigorous verification of the absolute dose delivery. Currently available dosimetric verification methods, such as film dosimetry in phantoms and ion chamber point dose verification, however, result in either integrated dose or relative dose distribution verification, and not absolute dose verification. Also, these methods are time-consuming, cumbersome, and error-prone.

In established EPID-based pre-treatment dose verification methods, integrated images are compared against dose images predicted by the treatment planning system (TPS). Complex dynamic therapy techniques, however, require a more detailed verification based on cine image series. Therefore, in such complex treatments it is not enough to compare the integrated images against predicted dose images. Instead, the acquired dose images, converted to absolute dose distributions, need to be compared with the predicted dose images in a time-resolved manner.

Currently available comparison methods, such as the two component gamma function, are not suitable for time-dependent (i.e., dynamic) data comparison. Therefore, the existing gamma function is also not suitable for comparing the acquired dose images with the predicted dose images in a time-resolved manner.

SUMMARY

The present disclosure provides systems, methods, and computer program products for electronic portal imaging device (EPID)-based pre-treatment dose verification for dynamic treatment plans that allow for comparison of absolute dose distributions with predicted dose distributions in a time-resolved manner.

The present disclosure also provides systems, methods, and computer program products for (EPID)-based pre-treatment dose verification for complex dynamic treatment plans, such as, but not limited to (IMRT) and (VMAT) treatment plans.

The present disclosure also provides systems, methods, devices, and computer program products for time dependent pre-treatment dose verification using electronic portal imaging devices (EPIDs) for dynamic treatments using both flattened and flattening filter free (FFF) beams.

The present disclosure also provides an (EPID) calibration model for converting measured dose distributions into absolute dose distributions.

The present disclosure also provides systems, methods, and computer program products for quantitative evaluation of dose distributions.

The present disclosure also provides systems, methods, and computer program products for evaluating dose distributions using a 4D time-dependent gamma function.

The present disclosure also provides a non-transitory computer-readable storage medium upon which is embodied a sequence of programmed instructions for quality control in a radiation therapy treatment system as disclosed herein, including a computer processing system, as disclosed herein, which executes the sequence of programmed instructions embodied on the computer-readable storage medium to cause the computer processing system to perform the steps of the methods as disclosed herein.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

FIG. 3 is a pixel sensitivity correction profile graph.

FIG. 4 is an off-axis ratio correction profile graph.

FIG. 5 is a diagram of energy deposition kernels.

FIG. 6 is a graph of measured and simulated point dose values.

FIG. 8 illustrates a method for checking deviations of resampled images according to various embodiments.

FIG. 11 illustrates a percentage of in-field area failing the gamma criterion according to various embodiments.

DETAILED DESCRIPTION

Figure 1:
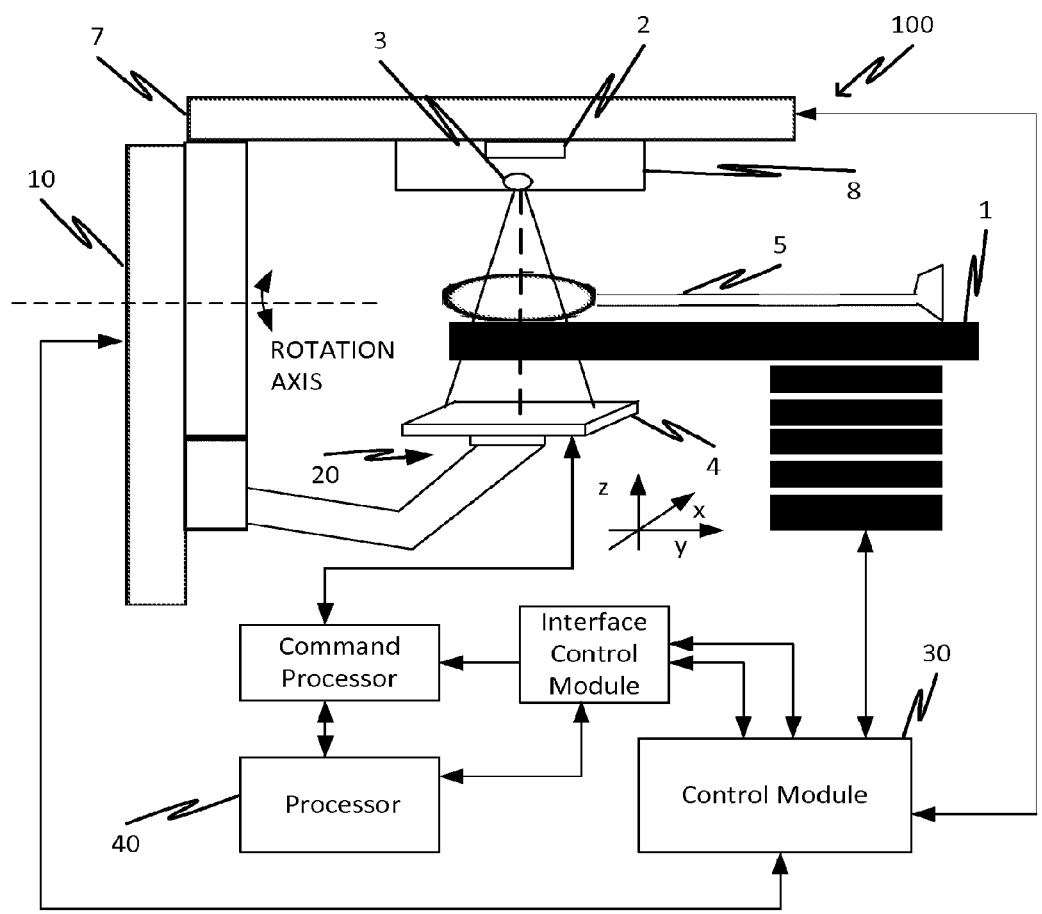
FIG. 1 is a perspective view of a dynamic radiation therapy system according to various embodiments of the invention.

FIG. 1 illustrates an exemplary radiation therapy treatment system 100 that can provide radiation therapy to a patient 5 positioned on a treatment couch 1, and allow for the implementation of various pre-treatment portal dosimetry verifications for quality assurance (QA) protocols. The radiation therapy treatment can include photon-based radiation therapy, particle therapy, electron beam therapy, or any other type of treatment therapy. In an embodiment, the radiation therapy treatment system 100 includes a radiation treatment device 10, such as, but not limited to, a radiotherapy or radiosurgery device, which can include a gantry 7 supporting a radiation module 8 which includes one or more radiation sources 3 and a linear accelerator (linac) 2 operable to generate a beam of kV or MV X-ray radiation. The gantry 7 can be a ring gantry (i.e., it extends through a full 360 degree arc to create a complete ring or circle), but other types of mounting arrangements may also be employed. For example, a static beam, or a C-type, partial ring gantry, or robotic arm could be used. Any other framework capable of positioning the radiation module 8 at various rotational and/or axial positions relative to the patient 5 may also be used.

The radiation module 8 can also include a modulation device (not shown) operable to modulate the radiation beam as well as to direct a therapeutic radiation beam toward the patient 5 and toward a portion of the patient which is desired to be irradiated. The portion desired to be irradiated is referred to as the target or target region or a region of interest. The patient 5 may have one or more regions of interest that need to be irradiated. A collimation device (not shown) may be included in the modulation device to define and adjust the size of an aperture through which the radiation beam may pass from the source 3 toward the patient 5. The collimation device may be controlled by an actuator (not shown) which can be controlled by a computer processing system 40 and/or a controller 30.

In an embodiment, the radiation therapy device is a kV or MV energy intensity modulated radiotherapy (IMRT) device. The intensity profiles in such a system are tailored to the treatment requirements of the individual patient. The intensity modulated radiotherapy fields are delivered with a multileaf collimator (MLC), which can be a computer-controlled mechanical beam shaping device attached to the head of the linear accelerator and includes an assembly of metal fingers or leaves. The (MLC) can be made of 120 movable leaves with 0.5 and/or 1.0 cm leaf width, for example. For each beam direction, the optimized intensity profile is realized by sequential delivery of various subfields with optimized shapes and weights. From one subfield to the next, the leaves may move with the radiation beam on (i.e., dynamic multileaf collimation (DMLC)) or with the radiation beam off (i.e., segmented multileaf collimation (SMLC). The device 10 can also be a tomotherapy device where intensity modulation is achieved with a binary collimator which opens and closes under computer control. As the gantry continuously rotates around the patient, the exposure time of a small width of the beam can be adjusted with the opening and closing of the binary collimator, allowing the radiation to be delivered to the tumor through the most preferred directions and locations of the patient.

The device 10 can also be a helical tomotherapy device which includes a slip-ring rotating gantry. The device 10 can also be an intensity modulated arc therapy device (IMAT) where instead of using rotating fan beams, rotational cone beams of varying shapes are used to achieve intensity modulation. The device 10 can also be a simplified intensity modulated arc therapy (SIMAT) device which uses multiple arcs, or a sweeping window arc therapy device (SWAT), where the (MLC) leaf positions sweep across the target planning volume (TPV) with rotation. The device 10 can also be a volumetric modulated arc therapy (VMAT) device where dose rate, beam aperture shape, and the speed of rotation can be continuously varied to deliver the prescribed dose to the target planning volume (TPV).

Although illustrative embodiments include (VMAT) as the treatment device 10, any type of intensity modulated radiotherapy (IMRT) device can be used. Each type of device 10 is accompanied by a corresponding radiation plan and radiation delivery procedure.

The device 10 further includes a portal dose imaging device 20 for acquiring digital images to be used for portal dosimetry verification. The portal dose imaging device 20 can be an electronic portal imaging device (EPID). The portal dose imaging device 20 can be placed at different locations, such as, on top of the treatment couch 1, or attached to the accelerator head 2, for example. The portal dose imaging device 20 can generate immediate 2D digital information. It can be a camera-based device, such as a camera-based (EPID), or an amorphous silicon based device, such as an amorphous silicon (EPID). The (EPID) 20 can also be a CCD-camera based (EPID), which is effectively an array of simultaneously integrating dosimeters with a dead time in between acquired frames of about 0.1 ms, for example. Another alternative is a flat panel imager (or amorphous silicon EPID), which offers good image quality, high optical transfer efficiency, large imaging area, and resistance to radiation.

An exemplary amorphous silicon imaging device that can be used is a aSi1000 EPID imager that has arrays of light sensitive amorphous-Si photodiodes arranged in 40×30 cm$^2$ active detector area 4 and has a maximum frame rate of 9.574 fps, each frame being a scan of the detector elements. The flat panel imager generally consists of picture elements (pixels) that register the amount of radiation that falls on them and convert the received amount of radiation into a corresponding number of electrons. The electrons are converted into electrical signals which are further processed using either the imaging device 20 or a computer 40. Such a configuration (i.e., digital imaging detector(s) positioned opposite the therapeutic source(s)) provides the ability to continuously and immediately capture the energy and intensity of the therapeutic radiation transmitted from each arc field segment and/or during a continuous arc beam delivery, in order to generate two-dimensional (2D) images of digitized X-ray measurements. Because the portal dose imaging device 20 generates immediate, 2D digital information, it facilitates 2D dosimetry at any gantry angle.

The computer 40 includes typical hardware such as a processor, and an operating system for running various software programs and/or communication applications. The computer can include software programs that operate to communicate with the radiation therapy device 10, and the software programs are also operable to receive data from any external software programs and hardware. The computer 40 can also include any suitable input/output devices adapted to be accessed by medical personnel, as well as I/O interfaces, storage devices, memory, keyboard, mouse, monitor, printers, scanner, etc. The computer 40 can also be networked with other computers and radiation therapy systems. Both the radiation therapy device 10 and the computer 40 can communicate with a network as well as a database and servers. The computer 40 is also adapted to transfer medical image related data between different pieces of medical equipment.

The system 100 can also include a plurality of modules containing programmed instructions which communicate with each other and cause the system 100 to perform different functions related to radiation therapy/surgery, as discussed herein, when executed. For example, the system 100 can include a treatment plan module operable to generate the treatment plan for the patient 5 based on a plurality of data input to the system by the medical personnel, the treatment plan including a predicted radiation dose distribution, a patient positioning module operable to position and align the patient 5 with respect to the isocenter of the gantry 7 for a particular radiation therapy treatment, an image acquiring module operable to instruct the radiation therapy device 10 to acquire images of the patient 5 prior to the radiation therapy treatment and/or during the radiation therapy treatment (i.e., in-vivo images), and/or to instruct other imaging devices or systems to acquire images of the patient 5.

The system 100 can further include a treatment delivery module operable to instruct the radiation therapy device 10 to deliver the treatment plan with or without the patient 5 in place, a converting module operable to convert the 2D portal images (EPIs) into 2D portal doses, an analysis module operable to compute comparisons between predicted and measured dose distributions, and a calculation module operable to calculate dose delivery errors. The analysis module can further include computational algorithms to quantitatively compare the measured and the predicted dose distributions in a time-resolved manner. The modules can be written in the C or C++ programming languages, for example. Computer program code for carrying out operations of the invention as described herein may also be written in other programming languages.

As part of the quality control protocol, for pre-treatment portal dosimetry verification, the radiation dose distribution delivered by the treatment fields is validated before starting the patient treatment. Patient treatment involves irradiating the patient with treatment beams (i.e., X-rays, for example) according to a prescribed delivery treatment plan. The prescribed delivery plan is developed using a treatment planning system (TPS) prior to the treatment phase, and involves developing a plan using special computer software to optimally irradiate the tumor and minimize dose to the surrounding normal tissue from different angles and planes. The treatment plan includes a trajectory (motion path) for the radiation beam computed to deliver a dose distribution that the treating physician finds acceptable, taking into account a variety of medical constraints. The beam trajectory is developed based on knowledge of the exact coordinates of the target within the anatomical structure, and the exact shape and size of the tumor or abnormality within the body. For arc therapy (e.g., dynamic treatment), a trajectory may be an arc, typically a single 360 degree, or a single 180 degree revolution, formed by the rotation of the treatment gantry about the patient.

To optimize arc delivery treatment plans, at the outset of the treatment planning process, a number of control points (CPs) along the trajectory are specified. Each control point (CP) is associated with a set of treatment parameters, including but not limited to, a set of (MLC) leaf positions, (MLC) shape, gantry rotation speed, gantry position, dose rate, and/or any other parameters. The number and position of the control points (CPs) may be set in any convenient manner, such as, but not limited to, by using the treatment planning software, or by the system operator. In an exemplary embodiment, the trajectory can include a single 180 degree arc trajectory and approximately 177 sequential control points (CPs), which means that there are 177 configurations that the linac 2 should conform to in order to deliver the planned treatment.

Figure 2:
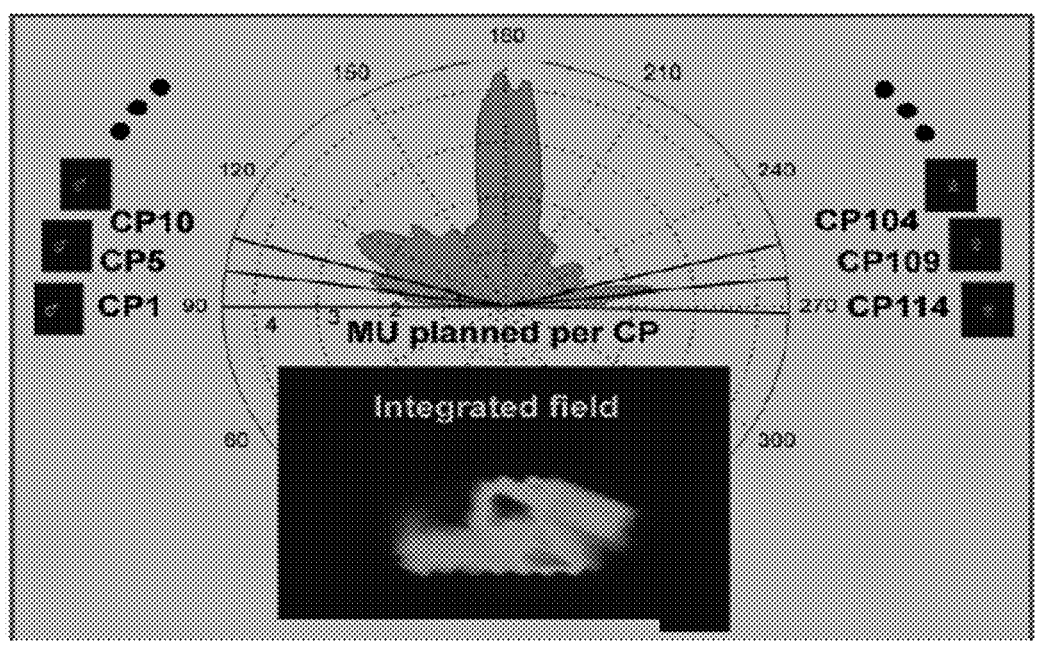
FIG. 2 illustrates predicted portal dose images generated per control point (CP) according to various embodiments.

Based on the treatment parameters, a dose distribution within the treatment volume is calculated for each control point (CP) by any number of techniques, such as, but not limited to, pencil beam convolution, or any other suitable algorithm. In order to generate a predicted portal dose image for an arc segment located between two consecutive control points ("predicted image per CP"), once the treatment plan is completed, the radiation dose distribution for each (CP) is associated with the corresponding gantry angle, (MLC) configuration, and monitor unit (MU) extracted from the system's RTPLAN file. The RTPLAN is a treatment planning module that can include a plurality of radiotherapy (RT) modules associated with the processor 40 that work together to address the requirements for transfer of treatment plans before or during a course of treatment. The modules can include information about the general treatment plan, prescription, tolerance tables patient setup, fraction scheme, beams, etc. By extracting the gantry angle, (MLC) configuration, and the monitor unit (MU) for each control point (CP) from the RTPLAN file and associating the extracted (CP) parameters with the corresponding calculated dose distributions for each (CP), each (CP) is in effect treated as a static field. By treating each (CP) as a static field, a predicted portal dose image for each field (i.e., for each CP) can be generated, as shown in FIG. 2. By generating a predicted dose image for each (CP), a sequence of 2D predicted portal dose images are obtained, each predicted portal dose image in the sequence corresponding to a respective (CP). The generated sequence of predicted portal dose images can be stored in the computer processor 40.

After the treatment planning, and before treatment delivery, the pre-treatment dose validation described herein is executed as part of the quality assurance protocol. The pre-treatment dosimetric validation process includes delivering the radiation beam, absent the patient, onto the EPID 20 as per the treatment plan, continuously measuring the delivered radiation dose, and comparing the measured dose with the predicted dose. A method to accomplish this pre-treatment dosimetric evaluation in a time-resolved fashion and in near real-time, the method includes the following steps: (1) during a continuous arc beam delivery, which could be a 180 degree arc for example, 2D portal images (EPIs) G'(x, y) are continuously acquired using the electronic portal imaging device (EPID) 20; (2) the acquired 2D portal images are converted into 2D absolute portal dose images (PDIs) $D_p(x, y)$ using a dosimetric calibration model described herein; (3) the image frames are resampled into respective time divisions corresponding to the treatment plan's control points (CPs) to obtain a sequence of 2D measured portal dose images, each measured portal dose image in the sequence corresponding to a respective (CP); and (4) each of the measured portal dose images are compared with corresponding predicted portal dose images using a time-dependent gamma evaluation function. Each of the enumerated steps are described in detail herein.

To generate the sequence of portal images, the EPID 20 receives data from different projection angles θ≤θ≤360° as the gantry 7 rotates, collects the transmitted radiation, and continuously generates two-dimensional (2D) digital portal images (EPI) G'(x, y). Each portal image (EPI) G'(x, y) is generated under the same condition as is planned for the actual treatment, but without the patient placed in the beam. The EPID images G'(x, y) are captured in a continuous dosimetric fashion without syncing the beam pulses and the EPID readout in order to provide a plurality of raw 2D portal images (i.e., a fluoroscopic image sequence). The system 100 can further include a frame grabber card (not shown) and associated hardware and software tools (not shown) which allow the raw image frames to be directly exported from the EPID to the computer 40 before any correction is applied. The system 100 further includes a synching module configured to associate the acquired image frames with the treatment information (i.e., plan identification, plan parameters, etc.), and to resample the image frames into correct time divisions corresponding to the treatment plans' control points (CPs).

The continuously acquired EPID images G'(x, y) are converted into 2D absolute dose sequences (i.e., dose film) using a dosimetric calibration model, as shown in eq. 2. The absolute portal dose images $D_p(x, y)$ so obtained represent absolute dose distributions at the plane of the EPID, and are obtained by converting gray scale pixel values to dose values or simulation of the gray scale pixel values. By continuously converting the measured EPID images G'(x, y) into absolute portal dose images (PDIs) $D_p(x, y)$, a sequence of measured absolute portal dose images is obtained. However, prior to converting the measured EPID images into absolute portal dose images, the measured EPID images G'(x, y) can be corrected for the non-uniform arm back-scatter present in certain support arm designs of the radiation device 10. The correction is done using an implementation of the convergent Van Cittert approximate deconvolution, shown in eq. 1.

$$G'(x,y)_{n+1} = G'(x,y)_n - \mu(G_{DD}(x,y) - (G'(x,y)_n \cdot AM(x,y) \otimes K_{BS}(i,j))) \quad (1)$$

Where n is an iteration number, $G'_{n+1}$ represents the convergent solution and μ is a relaxation factor. $G_{DD}$ represents the initial EPID image which is corrected for dead pixels and dark field offset (i.e., the signal from the EPID when no radiation is incident on it). $G_{DD}$ is used as the initial estimate (i.e., $G'_{n=0} = G_{DD}$). AM is the mask of the EPID arm, $K_{BS}$ is the backscatter kernel, and ⊗ denotes a convolution. The coordinates (x, y) are relative to the beam axis where (i, j) are relative to the kernel center.

The absolute portal dose images $D_p(x, y)$ are then generated using the back-scatter corrected portal images and the following portal dose reconstruction algorithm (i.e., EPID calibration model):

$$D_p(x,y) = (C_F^{-1} \cdot G(t_{rad})^{-1} \cdot G'(x,y) \cdot PS^{-1}(h,v) \cdot OAR^{-1}(x,y) \otimes^{-1} K_F(i,j)) \otimes^{-1} K_P(i,j) \quad (2)$$

Thus, each absolute portal dose image $D_p(x, y)$ is obtained by correcting each corresponding measured (and arm-scatter corrected) EPID image G'(x, y) for ghosting ($G(t_{rad})$), pixel sensitivity (PS), and off-axis ratio (OAR), followed by deconvolving with in-field and penumbra energy deposition kernels ($K_F$ and $K_P$ respectively). $C_F$ is the absolute conversion factor of EPID pixels to dose under a reference condition.

The coordinates (h, v) are the pixel index on the EPID. Each of the correction factors are described below.

1. A Dead Pixel (DP) Correction.

Over time/use a small number of individual EPID pixels are permanently damaged and stop responding to radiation. To correct for these dead pixels, each one can be identified using a threshold bitmask, and an average value, derived from the surrounding pixels, can be used to replace the erroneous value. All EPID frames can be corrected for dead pixels.

2. The Dark Field Correction ($G_{DD} = G_{raw} - DF$).

This is to remove any persistent signal from the EPID images which is present when no radiation is incident on it. This is the dark field (DF) image, also known as the offset image. The noiseless DF image can be obtained by averaging 100 frames without a beam. This correction can be applied automatically when using clinical acquisition software. All raw greyscale EPID images ($G_{raw}$) can be corrected by subtracting the DF image.

3. Support Arm Backscatter (ABS).

This correction is to obtain quantitative images as the design of the EPID support arm may result in non-uniform backscatter. The correction is applied via eq. 1 shown above, but to derive the parameters of the back scatter kernel ($K_{BS}$) and the vertices of the arm mask (AM), an iterative process can be applied. As an exemplary process, a number of fields are measured and an initial estimation of the shape of the support arm can be provided as a binary mask along with an initial guess of the single Gaussian backscatter kernel. A backscatter corrected image can be generated of any field using the resultant mask and backscatter kernel and the convergent method shown in eq. 1.

4. Pixel Sensitivity (PS).

This refers to the fact that the response to a uniform photon fluence varies from pixel to pixel. The relative difference can be corrected by using a pixel sensitivity map. A pixel sensitivity map can be generated by first exposing different areas of the EPID to the same portion of a beam, which has a constant beam profile and spectrum. Flood images (FF image) can also be acquired. A composite cross-line 1D profile can be formed from the central cross-line 2 cm, for example, of each field to obtain the sensitivity of the central row of pixels. The ratio profile (RP) of the beam can be obtained by dividing the corresponding row of pixels of the FF image with the composite 1D pixel sensitivity profile. A profile of the FF image is shown as the dotted line in FIG. 3. Noises and discontinuities, if present, can be reduced by fitting a 2nd order polynomial function to the data and extending beyond the measured region shown as the dashed line in FIG. 3. As the beam is assumed to be radially symmetric, a 2D ratio image can be obtained by sampling the 1D (RP) in a radial fashion. The 2D pixel sensitivity map can then be obtained by dividing the FF image by the ratio image and scaling the values to be relative to the central on-axis value. A profile of the obtained sensitivity map can be shown as the solid line in FIG. 3. The FF image contains (OAR), the beam profile (BP), and (PS). The ratio image contains only the (OAR) and (BP). By dividing the two images, the (PS) can be obtained. All further calibration images can be corrected for pixel sensitivity before additional calculation.

5. The Off-Axis Ratio (OAR).

This is the relative EPID response due to the change in beam spectrum off-axis. The off-axis variation in pre-treatment beams is primarily due to the flattening filter and target, but also includes inherent beam features and scatter. This variation can be corrected to obtain reliable distributions further away from the central beam axis. Once corrected for DP, DF, ABS, and PS, the EPID images still contain the BP and the OAR. While keeping the EPID static, a number of rectangular fields can be imaged, each shifted 2 cm from the last in the cross-line direction. A composite cross-line profile can be formed using the central cross-line 2 cm of pixels for each field. An ionization chamber, for example, can be used to obtain the corresponding central field dose for each of the fields and a surrogate beam profile can be created from these values. The 1D OAR profile can then be obtained by dividing the composite cross-line profile by the ionization chamber obtained surrogate beam profile. Again a 2nd order polynomial function can be fitted to the 1D OAR (shown in dashed in FIG. 4), extended beyond the measured region (to encompass all possible positions of the EPID) and sampled in a radial fashion to obtain a 2D OAR distribution. All further calibration images can be corrected for OAR before additional calculation.

6. The Absolute Conversion Factor (CF).

This is the absolute conversion between EPID response and absolute ion chamber measurements. All other correction factors are relative to this measurement.

7. Field Size Energy Deposition Kernels ($K_F$ and $K_p$).

Due to the scatter from the EPID itself, the pattern of energy deposition should be known so that the incident point dose image can be obtained. As the energy deposition pattern varies for changing field sizes, due to changes in scatter from both the linac head and the EPID itself, a deposition pattern that can account for the change in field size is required. This can be achieved using energy deposition kernels for the in-field and penumbra regions, and a single out of field factor. To derive the parameters for the energy deposition kernels, EPID and ionization chamber measurements can be performed for each energy and source-detector distance (SDD). A plurality of on-axis fields can be imaged with the EPID. The fields can be measured at their field centre separately using an ionization chamber to obtain a central 1D in-line profile of each field. As illustrated in FIG. 5, the in-field kernel can include 2 radially extended exponential functions, one narrow peaked, and one broader, shallower function. Field masks can be created for the in-field, and out-of-field regions.

Figure 7:
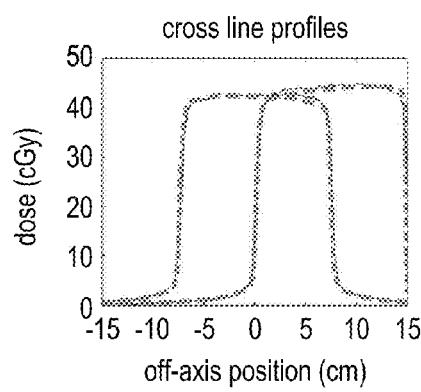
FIG. 7 is a graph of measured and simulated dose profiles for on and off-axis radiation fields.

A portal dose image (PDI) is created for each of the fields imaged using the EPID. This can be done by applying all corrections (DP, DF, ABS, PS, OAR, and CF) to the measured EPID images. Then using initial, arbitrary, values for the kernel parameters, each field is deconvolved with the kernels resulting in a portal dose image (PDI). A central field dose can be sampled and compared to the ionization chamber measured values for those fields, shown in FIG. 6. From each field (on and off axis) PDI, a 1D in-line profile can be sampled and compared to the scanning ionization chamber measured values, shown in FIG. 7. By allowing the parameters of both kernels to vary ($K_f$ and $K_p$ in eq. 2), an iterative process can be used to obtain the best fitting values for each by minimizing the deviations with a weighting process. Once kernel parameters are found, they can be used to deconvolve any open field at that energy and SDD.

8. The Ghosting Correction ($G(t_{rad})$).

This compensates for any non-linearity in EPID response to varying MU. There are different mechanisms that contribute to the non-linearity. Charge trapping in the photodiode surface or bulk modulus can increase image lag (residual images from previous frames are visible in the current frame) or can change the electric field within the photodiode, increasing the sensitivity of the detector (the panel's response increases as it is irradiated). The influence of these effects differs for the different constructions of EPID.

The ghosting correction for the method presented here has little or no influence on the resulting images. As a result, the correction is not applied for (VMAT) or dynamic (IMRT) fields but is still applied to static field treatments.

Control Point Synchronisation

Using the EPID calibration model as described above, absolute dose portal images (i.e., measured portal dose images) are obtained for the EPID images continuously acquired during the single 360 degree arc gantry rotation and radiation field delivery. In order to compare the measured portal dose images with the predicted portal dose images, which are the predicted dose images at control points (CPs), the 2D absolute portal dose images $D_p(x, y)$ are grouped into corresponding control point (CP) divisions. The (CP) grouping is facilitated by two sets of data. One set of data is contained in the linac's trajectory log files, and another set of data is contained in the EPID frame header. The linac trajectory log files contain, among other parameters, a sampling of the (CP), (MLC) position, gantry angle, and (MU) every 20 ms, for example. The EPID frame header data contains a sampling of (MU) and gantry angle every ~104 ms, for example. The trajectory log files can be used to divide the treatment plan delivery time into (CP) divisions. Further, the beam-on time can be synchronised between the log files and the EPID frames using the sampled (MU) values. The EPID frames can then be resampled using the timing data from the EPID frame file headers into control point (CP) sized portal dose images (PDIs). By resampling the EPID frames, the measured absolute portal dose images, are grouped into corresponding (CPs). The so obtained series of measured absolute portal dose images, each of the measured absolute portal dose images in the series corresponding to a respective (CP), can be stored in the computer 40. The reliability of the resampling can be checked using the differential (MU) values in both the trajectory log file and the EPID frame header. Both sets of values come from the linac's monitor chamber and so any large deviations can be easily detected, as shown in FIG. 8.

The Time Dependent Gamma Comparison

Figure 9:
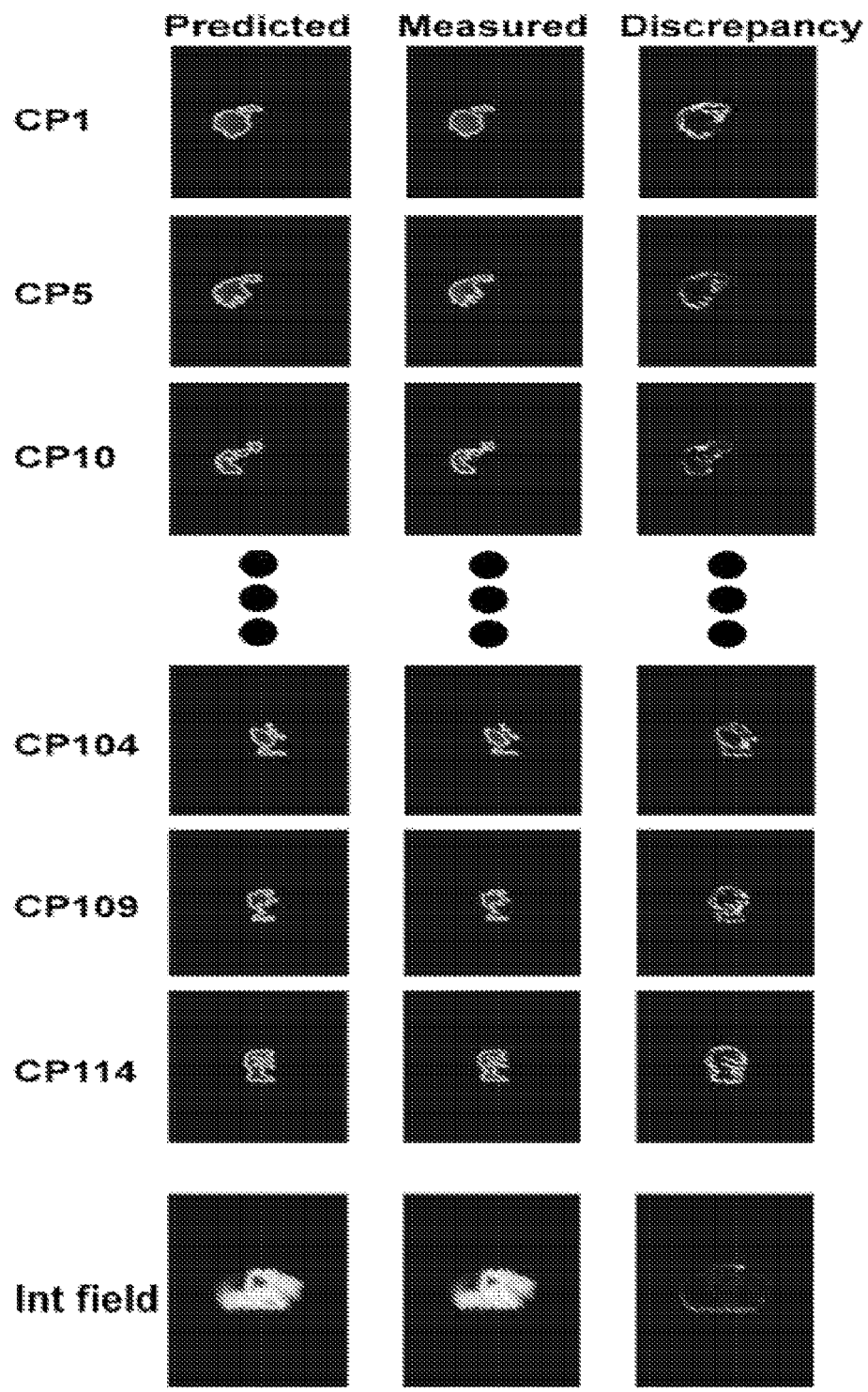
FIG. 9 illustrates a method for direct comparison between predicted and measured radiation doses per control points (CPs) according to various embodiments.

Since both, the measured and the predicted portal dose images, are grouped into corresponding (CPs), for each (CP), a direct comparison between the measured and the predicted dose can be made, as shown in FIG. 9. Using a comparison algorithm, the differences between each of the predicted and corresponding measured portal dose images can be determined, and the discrepancies between the corresponding predicted and measured portal dose images be displayed and further evaluated, as illustrated in FIG. 9. The time-dependent comparison described herein, therefore, allows for the detection of discrepancies between the measured and predicted dose distributions that otherwise would have been averaged out (i.e., if the images were integrated instead of grouping them in time divisions). As shown in FIG. 9, integrated predicted portal dose images as well as integrated measured portal dose images can also be generated and compared with each other. However, as shown in FIG. 9, the time-dependent comparison highlights discrepancies that are not shown when only the integrated images are compared.

Instead of a direct comparison between the measured and corresponding predicted portal dose images, a time-dependent gamma function described herein can be used to evaluate the differences between the predicted and measured portal dose images.

Gamma evaluation is a method generally used to quantitatively compare dose distributions. The conventional gamma method uses a comparison between a measured and predicted dose distribution. Generally, the gamma evaluation method combines a dose difference criterion with a distance-to-agreement (DTA) criterion which makes it a suitable method for both low and high dose gradient regions. Dose distributions can be subdivided into regions of low and high dose gradients, each with a different acceptance criterion. High dose gradients could be regions defined as pixels with maximum relative dose differences above 10% for neighboring pixels, for example. In high dose gradient regions a small spatial error either in the calculation or the measurement results in a large dose difference between measurement and calculation. Dose difference in high dose gradient regions may therefore be unimportant, and the concept of distance-to-agreement (DTA) distribution is used to determine the acceptability of the dose calculation. The distance-to agreement (i.e., geometric) (DTA) criterion (i.e., parameter) is the distance between a measured data point and the nearest point in the predicted dose distribution that exhibits the same dose.

To determine dose variations using the gamma evaluation method, the relative dose difference between portal dose images (PDIs) is calculated by comparing each point in the measured dose distribution with the same point in the predicted dose distribution. A dose-difference distribution can be displayed that identifies the regions where the predicted dose distributions disagree with the measurement. The gamma evaluation method is a technique that unifies dose distribution comparisons using acceptance criteria. The measure of acceptability is the multidimensional distance between the measurement and predicted points in both the dose and the physical distance. The gamma value is a numerical quality index that serves as a measure of disagreement in the regions that fail the acceptance criteria and indicates the calculation quality in regions that pass. Gamma values below unity indicate agreement within the passing criteria. The passing criteria for dose difference criterion and the geometric (Distance to Agreement, DTA) criterion is generally 3% and 3 mm, respectively. The gamma value is calculated based on these criteria.

Thus, for the conventional two component gamma function, a point is taken in the measured dose, and compared to all points in the predicted dose that fall within a geometrical search box defined by the (DTA). The point in the predicted dose with the lowest gamma index is considered the best match.

For example, for two static 3D dose distributions, a dose which is predicted and is therefore labelled the referenced dose (or searched dose), and a measured dose which is labelled the compared dose, the gamma index ($\gamma$) can be obtained for a point $p_{com}$ in the compared dose via eq. 3:

$$(p_{com}) = \min\left\{\sqrt{\frac{d^2(p_{com}, sp_{ref})}{DTA^2} + \frac{\delta^2(p_{com}, sp_{ref})}{DD^2}}\right\} \forall \{sp_{ref} \in \hat{v}\} \quad (3)$$

Where $p_{com}$ is a fixed geometrical point of a voxel in the compared dose; $sp_{ref}$ is any point within the search sphere $\upsilon$ (whose radius=DTA) in the reference dose; and $d(p_{com}, sp_{ref})$, and $\delta(p_{com}, sp_{ref})$ are the geometrical distance and dose difference between points $p_{com}$ and $sp_{pred}$, respectively. The $\gamma$ index is calculated for each voxel in the search sphere $\upsilon$ and the lowest value kept as the $\gamma$ value for point $p_{com}$. The process is repeated for every voxel in the measured dose until a 3D gamma ($\gamma$) index with the same dimensions as the measured dose is produced.

For quickly changing dynamic data, such as 2D/3D dose distributions of varying MLC defined fields, a situation occurs, similar to the high dose gradient regions described above. For each time point, a toxel may find itself inside or outside of the primary field resulting in a high dose gradient in time. This high dose time gradient is also omnipresent in methods that employ a varying dose-rate scheme, such as VMAT. If a static comparison is used such as the method described in eq. 3, small discrepancies in timing, arising from imperfect synchronization or delivery discrepancies will result in large and persistent differences between measurement and calculation. In order to correctly compare in a time-wise fashion, the general gamma function is expanded to take into consideration an additional criterion. The additional criterion is the time to agreement (TTA) criterion, which is selected separately from the geometric (DTA) criterion. The time-dependent gamma index then becomes:

$$\gamma(p_{com}, t_{com}) = \min\left\{\sqrt{\frac{d^2(p_{com}, sp_{ref})}{DTA^2} + \frac{\delta^2(p_{com}, sp_{ref})}{DD^2} + \frac{t^2(p_{com}, sp_{ref})}{TTA^2}}\right\} \forall \{sp_{ref} \in v\} \quad (4)$$

Where $t(p_{com}, sp_{ref})$ is the time difference between points $p_{com}$ and $sp_{ref}$. The $\gamma$ index is calculated for each voxel in the 4D search volume $\upsilon$ and the lowest value kept. The process is repeated for every toxel (time dependent voxel), meaning it is repeated for every voxel in the measured dose at every available time within the data. The passing criteria for dose difference criterion, the geometric (DTA) criterion, and the time (TTA) criterion then becomes e.g. 3%, 3 mm, and 3 s, respectively. The gamma value is calculated and compared with these criteria.

To decrease the time required to calculate a gamma distribution, an ordered search box and an early stopping criterion can also be applied. This involves pre-calculating the distances (d) of each vector in the search box, disregarding vectors that fall outside the region of interest (ROI) sphere, and then the $\gamma$ index is calculated using the search box in ascending order of distance, stopping when $(d^2/DTA^2)$ exceeds the smallest $((d^2/DTA^2)+(\delta^2/DD^2))$ value found. Using an (ROI) that is much larger than the (DTA), allows gamma values to be calculated for two areas: first, the pixels passing the gamma criterion (within unity); and second, a band of pixels which fail the gamma criterion (exceeding unity). The second area can provide a measure of failure to be viewed for failing pixels which may inform interpretation.

For a time dependent gamma function, the search box is ordered in ascending value of $((d^2/DTA^2)+(t^2/TTA^2))$ and the $\gamma$ calculation stops when $((d^2/DTA^2)+(t^2/TTA^2))$ exceeds the smallest $((d^2/DTA^2)+(t^2/DD^2)+(t^2/TTA^2))$ found. As the number of vectors is largely increased for dynamic data, a more aggressive filtering can be imposed on the search box in order to achieve reasonable calculation times. Vectors that exceed 2× unity, based on their position and time alone, i.e. $((d^2/DTA^2)+(t^2/TTA^2))>2$ can be discarded. This results in far fewer search vectors than discarding vectors based on the region of interest (ROI) and time of interest (TOI) alone while still having a measure of failure outside unity.

To reduce the calculation time, the time-dependent gamma function can be applied on a graphics processing unit (GPU) as well as a central processing unit (CPU).

Figure 10:
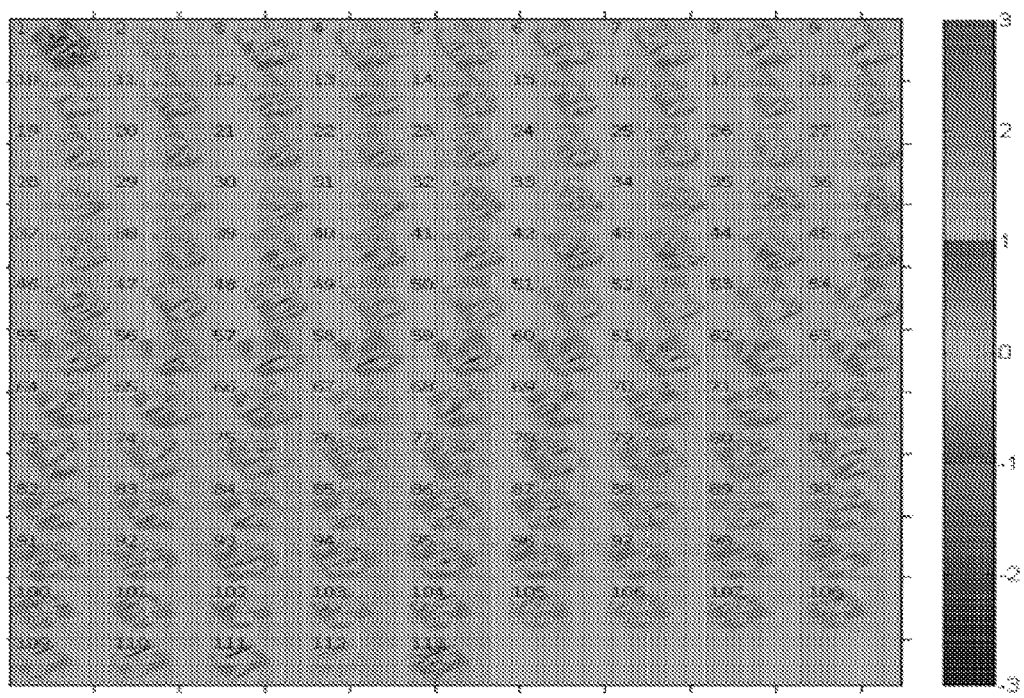
FIG. 10 illustrates a gamma distribution between measured and predicted doses per control points (CPs) according to various embodiments.

Since the time-dependent 4D gamma function uses criteria from each dimension and searches through the data within the allowed degrees of freedom, it can return an easier to read unity map, as shown in FIG. 10. As shown in FIG. 11, assessment can be made on the amount of toxels (voxels that change over time) exceeding unity to gauge the quality of the treatment delivery.

The time-dependent gamma function can provide a practical and reliable comparison model to robustly compare the measured dose distribution with a predicted dose distribution in a time-dependent manner. The time-dependent gamma evaluation method can thus be used for automated error detection using EPIDs.

Figure 12:
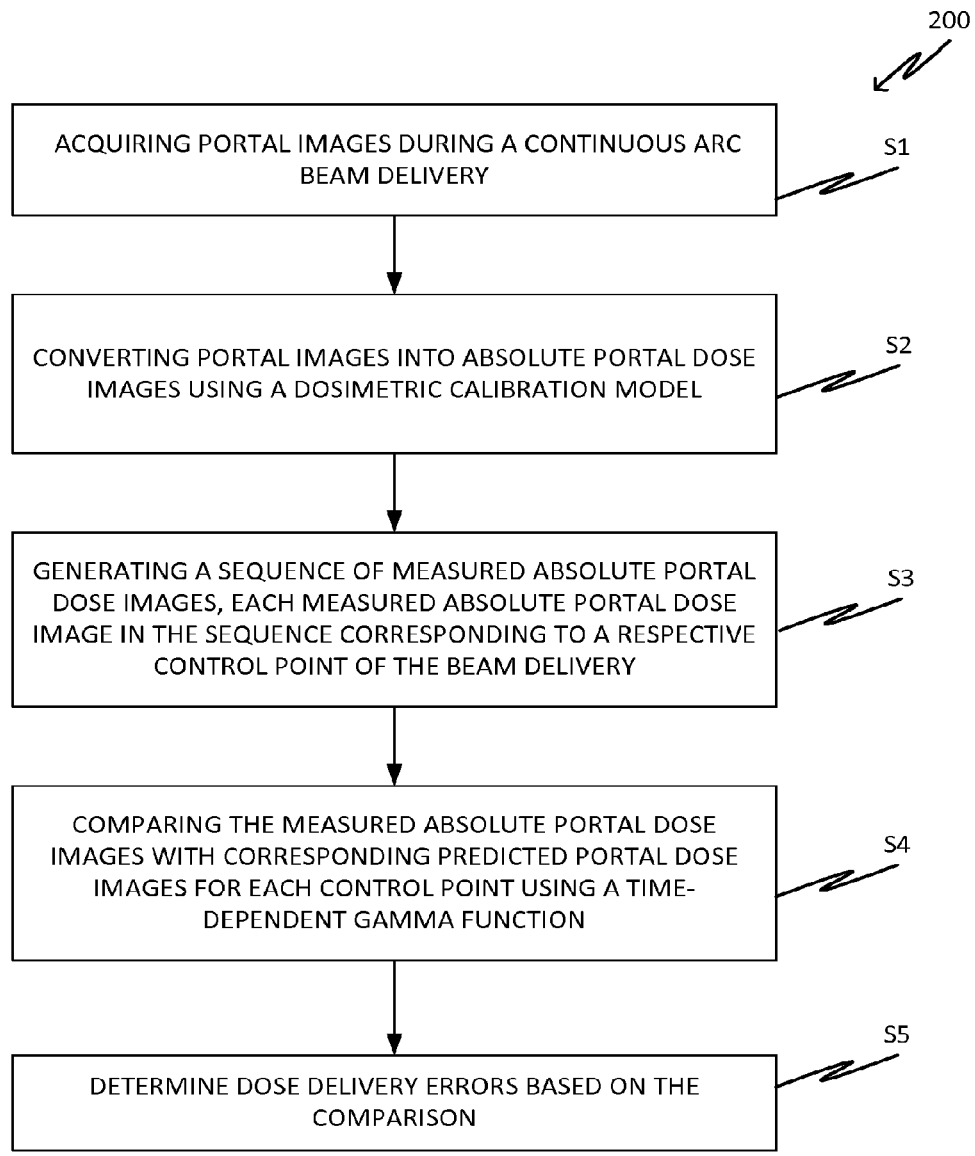
FIG. 12 is a flow chart of a dosimetric evaluation procedure according to various embodiments.

The steps of the time-dependent dosimetric verification process 200 described herein is as shown in FIG. 12. In Step 1 (S1), 2D portal images are continuously acquired during a continuous arc beam delivery using the electronic portal imaging device (EPID) 20. In Step 2 (S2), the acquired 2D portal images are converted into 2D absolute portal dose images (PDIs) $D_p(x, y)$ using a dosimetric calibration model described herein. In Step 3 (S3) the image frames are resampled into respective time divisions corresponding to the treatment plan's control points (CPs) to obtain a sequence of 2D measured portal dose images, each measured portal dose image in the sequence corresponding to a respective (CP). In Step 4 (S4), each of the measured portal dose images is compared with a corresponding predicted portal dose image using a 4D time-dependent gamma evaluation function, and in Step 5 (S5), the dose delivery errors are determined based on the comparison by assessing the amount of toxels (voxels that change over time) exceeding unity.

In operation, the series of predicted portal dose images can be stored as a first data set mapped as a first 4D array including positional information and time information of the points in the predicted portal dose images, and the series of measured portal dose images can be stored as a second data set mapped as a second 4D array including positional information and time information of the points in the measured portal dose images. The positional information can include spatial locations of the predicted and measured radiation fields, and the time information can include the delivery times of the predicted and measured radiation fields. The comparing of measured and predicted dose distributions then includes comparing the first and second data sets using a 4D time-dependent gamma evaluation method by which the positional differences between corresponding points in the first and second data sets and the time differences between corresponding points in the first and second data sets are measured.

A non-transitory computer readable medium can be used to store the software or programmed instructions and data which when executed by a computer processing system 40 causes the system to perform various methods of the present invention, as discussed herein. The executable software and data may be stored in various places, including, for example, the memory and storage of the computer processing system 40 or any other device that is capable of storing software and/or data.

Accordingly, embodiments of quality control systems, methods and computer program products for time-dependent pre-treatment dosimetric evaluations have been disclosed. Many alternatives, modifications, and variations are enabled by the present disclosure. Features of the disclosed embodiments can be combined, rearranged, omitted, etc. within the scope of the invention to produce additional embodiments.

Embodiments also provide time-dependent pre-treatment dosimetric evaluation methods for an arc-based radiation therapy device, comprising: generating a sequence of portal dose images based on images continuously acquired during beam delivery according to a treatment plan, each portal dose image in the sequence corresponding to a measured dose delivered at a predetermined time interval of the treatment plan; for each predetermined time interval, comparing the generated portal dose image with a corresponding predicted portal dose image; and evaluating dose delivery based on the comparison.

Embodiments also provide methods for verifying quantities of interest of a radiation beam in an arc-based radiation therapy device, comprising: continuously acquiring portal images during a continuous arc beam delivery using the electronic portal imaging device (EPID); converting the acquired portal images into absolute portal dose images using a dosimetric calibration model; resampling the absolute portal dose images into respective time divisions corresponding to a treatment plan's control points (CPs) to obtain a sequence of measured portal dose images, each measured portal dose image in the sequence corresponding to a respective (CP); comparing each of the measured portal dose images in the sequence with corresponding predicted portal dose images using a 4D time-dependent gamma evaluation function; and determine dose delivery errors based on the comparison by assessing the amount of voxels that change over time exceeding unity.

Embodiments also provide systems for verifying quantities of interest of a radiation beam in an arc-based radiation therapy device including a gantry, comprising: a portal imaging device configured to measure incident radiation dose from predetermined radiation fields corresponding to an arc segment of the gantry and to generate a series of two-dimensional (2D) absolute portal dose images using a calibration model; and a processing device operably connected to the portal dose imaging device and configured to store the series of 2D absolute portal dose images in a first 4D array having spatial locations and time of delivery of the predetermined radiation fields as dimensions, the processing device being further configured to store a series of predicted 2D portal dose images in a second 4D array having spatial locations and time of delivery of predicted radiation fields as dimensions; wherein the processing device is further configured to compare points in the first 4D array with corresponding points in the second 4D array using a 4D gamma evaluation method, the gamma evaluation method including dose differences, spatial differences, and time differences between corresponding points in the first and second 4D arrays as parameters, wherein errors in the quantities of interest are determined based on the comparison.

Embodiments also provide a non-transitory computer-readable storage medium upon which is embodied a sequence of programmed instructions for quality control in a radiation therapy treatment system as disclosed herein, including a computer processing system, as disclosed herein, which executes the sequence of programmed instructions embodied on the computer-readable storage medium to cause the computer processing system to perform the steps of the methods as disclosed herein.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents.

What is claimed is:

1. A dosimetric evaluation method, comprising:
generating a sequence of portal dose images, the portal dose images in the sequence corresponding to measured radiation doses delivered according to a radiation treatment plan;
comparing the portal dose images generated with corresponding predicted portal dose images using a time-dependent gamma evaluation method; and
evaluating radiation dose delivery based on the comparison.

2. The method of claim 1, wherein the measured radiation doses are delivered at predetermined time intervals of the radiation treatment plan, and the comparing includes comparing the portal dose images generated for respective time intervals with corresponding predicted portal dose images.

3. The method of claim 2, wherein the time intervals correspond to respective control points (CPs) of the radiation treatment plan.

4. The method of claim 1, wherein the comparing comprises using the time-dependent gamma evaluation method to calculate dose differences, spatial differences, and time differences between points in the measured portal dose images and corresponding points in the predicted portal dose images.

5. The method of claim 1, wherein the evaluating includes determining dose delivery errors.

6. A method for verifying quantities of interest of a delivered radiation beam, comprising:
acquiring portal dose images during radiation beam delivery;
resampling the acquired portal dose images into respective time divisions corresponding to a radiation treatment plan's control points (CPs) to obtain a sequence of measured portal dose images, the measured portal dose images in the sequence corresponding to respective control points (CPs);
comparing the measured portal dose images in the sequence with corresponding predicted portal dose images using a time-dependent gamma evaluation method; and
determining dose delivery errors based on the comparison.

7. The method of claim 6, wherein the comparing comprises using the time-dependent gamma evaluation method to calculate dose differences, spatial differences, and time differences between points in the measured portal dose images and corresponding points in the predicted portal dose images.

8. The method of claim 7, wherein the comparing includes computing a time-dependent gamma error matrix based on a gamma error function including time as a fourth dimension.

9. The method of claim 6, wherein the evaluating includes determining dose delivery errors.

10. A system for verifying a quantity of interest of a radiation beam, comprising:
a portal imaging device configured to measure incident radiation dose from predetermined radiation fields and to generate a series of portal dose images; and
a processing device operably connected to the portal dose imaging device and configured to store the series of portal dose images in a first data array having spatial locations and time of delivery of the predetermined radiation fields as dimensions, the processing device being further configured to store a series of predicted portal dose images in a second data array having spatial locations and time of delivery of predicted radiation fields as dimensions,
wherein the processing device is further configured to compare points in the first data array with corresponding points in the second data array using a 4D gamma evaluation method, the gamma evaluation method including dose differences, spatial differences, and time differences between corresponding points in the first and second data arrays as parameters, and
wherein errors in the quantities of interest are determined based on the comparison.

11. The system of claim 10, wherein the quantity of interest is of a radiation beam used in an arc-field radiation therapy device.

12. The system of claim 11, wherein the arc-field radiation therapy device is one of an intensity modulated radiation therapy device and a volumetric modulated arc therapy device.

13. The system of claim 10, wherein the portal imaging device is an electronic portal imaging device (EPID).

14. The system of claim 10, wherein the quantity of interest is radiation dose.

15. A system including a radiation therapy device and a computer processing system which executes a sequence of programmed instructions embodied on a computer-readable storage medium to cause the computer processing system to:
initiate radiation beam delivery in the radiation therapy device according to a radiation treatment delivery plan;
acquire portal dose images during the radiation beam delivery;
resample the portal dose images into respective time divisions corresponding to the radiation treatment plan's control points (CPs) to obtain a sequence of measured portal dose images, each measured portal dose image in the sequence corresponding to a respective control point (CP);
compare the measured portal dose images in the sequence with corresponding predicted portal dose images using a time-dependent gamma evaluation method; and
determine radiation dose delivery errors based on the comparison.

16. The system of claim 15, wherein the time-dependent gamma evaluation method includes a 4D evaluation method including time as the fourth dimension.

17. The system of claim 15, wherein the comparing comprises using the time-dependent gamma evaluation method to calculate dose differences, spatial differences, and time differences between points in the measured portal dose images and corresponding points in the predicted portal dose images as parameters.

18. The system of claim 17, further including storing the predicted portal dose images as a first data set including positional information and time information of the points in the predicted portal dose images as parameters, and storing the measured portal dose images as a second data set including positional information and time information of the points in the measured portal dose images as parameters.

19. The system of claim 18, wherein the positional information includes spatial locations of the predicted and measured radiation fields, and the time information includes the times of the predicted and measured radiation fields, and wherein the comparing includes comparing the first and second data sets using the time-dependent gamma evaluation method.

20. The system of claim 19, wherein the comparing includes computing a time-dependent gamma error matrix based on a gamma error function:

$$\gamma(p_{com}, t_{com}) = \min\left\{\sqrt{\frac{d^2(p_{com}, sp_{ref})}{DTA^2} + \frac{\delta^2(p_{com}, sp_{ref})}{DD^2} + \frac{t^2(p_{com}, sp_{ref})}{TTA^2}}\right\} \forall \{sp_{ref} \in v\}  \quad 5$$

wherein the gamma value γ in the gamma error matrix is a minimum value of a positional metric and a time metric indicating a measure of acceptability of a quantity of interest.

\* \* \* \* \*